(12) United States Patent
Newton et al.

(10) Patent No.: US 7,674,780 B2
(45) Date of Patent: Mar. 9, 2010

(54) IRON SUCROSE COMPLEXES AND METHOD OF MANUFACTURE THEREOF

(75) Inventors: Christopher Benny Newton, Plainsboro, NJ (US); Jagadeesh Babu Rangisetty, Lawrenceville, NJ (US)

(73) Assignee: Navinta LLC, Ewing, NJ (US)

( * ) Notice: Subject to any disclaimer, the term of this patent is extended or adjusted under 35 U.S.C. 154(b) by 1571 days.

(21) Appl. No.: 10/889,124

(22) Filed: Jul. 12, 2004

(65) Prior Publication Data

US 2005/0209187 A1 Sep. 22, 2005

Related U.S. Application Data

(60) Provisional application No. 60/553,712, filed on Mar. 16, 2004.

(51) Int. Cl.
*A61K 31/70* (2006.01)
*A61K 31/7016* (2006.01)
*A61K 31/715* (2006.01)
*C07H 1/00* (2006.01)
*C07H 3/04* (2006.01)

(52) U.S. Cl. ............... 514/53; 514/54; 536/123.13; 536/123.1; 536/124

(58) Field of Classification Search ............ 514/53, 514/54; 536/123.13, 123.1, 124
See application file for complete search history.

(56) References Cited

U.S. PATENT DOCUMENTS

| 2,820,740 | A | 1/1958 | London et al. |
| 2,885,393 | A | 5/1959 | Herb et al. |
| 4,994,283 | A | 2/1991 | Mehansho et al. ......... 426/74 |
| 6,537,820 | B2 | 3/2003 | Beck et al. ......... 436/84 |
| 2002/0076821 | A1 | 6/2002 | Beck et al. ......... 436/74 |
| 2003/0153086 | A1 | 8/2003 | Beck et al. ......... 436/74 |
| 2003/0216566 | A1 | 11/2003 | Kumari et al. ......... 536/123.13 |
| 2005/0037996 | A1 | 2/2005 | Beck et al. ......... 514/59 |

FOREIGN PATENT DOCUMENTS

| CS | 245379 B1 * | 9/1986 |
| GB | 1133863 | 11/1908 |
| GB | 694452 | 7/1953 |
| IN | 187116 | 2/2002 |
| IN | 187116 A * | 2/2002 |
| WO | WO 03/098564 | 11/2003 |
| WO | WO 2004/019032 | 3/2004 |
| WO | WO 2005/000210 A2 | 1/2005 |

OTHER PUBLICATIONS

Perry's Chemical Engineers' Handbook (7th Edition) Edited by: Perry, R.H.; Green, D.W. © 1997 McGraw-Hill, pp. 22:73-74.
Kirk-Othmer Encyclopedia of Chemical Technology Copyright © 2003 by John Wiley & Sons, Inc. Article Online Posting Date: Mar. 14, 2003, pp. 321-397.
Spiro et al., The Hydrolytic Polymerization of Iron (III), *J. Am. Chem. Soc.*, 88:12, 1966, 2721.
Dangre, Arjun J., Sugar-ferric Chloride Complexes, *Journal of the University of Poona, Science and Technology* (1974), 46, 47-56.
Singh et al., Studies on Iron-Sucrose Chelate Formation and Development of Brown Colour, *Journal of the Indian Chemical Society* (1999),76(4), 231-232.
Computer DERWENT record 1997-226867 abstracting Chinese patent CN 1097989; Tong et al., Cane Sugar FE, Preparing Process and Preparation Thereof, Feb. 1, 1995.
Patent Abstracts of Japan, abstracting Japanese patent publication No. JP2000239154A2: Internal Medicine Composition Containing Iron Compound, Sep. 5, 2000.
STN Abstract: Accession No. 2004: 1026272 CAPLUS; Document No. 141: 416131; Title: An improved process for preparing saccharated iron oxide in powder form for use in tablets as well as for syrup preparation; Baburao, Telang Ramesh. IN 187116, Sep. 2, 2002.

* cited by examiner

*Primary Examiner*—Shaojia Anna Jiang
*Assistant Examiner*—Michael C Henry
(74) *Attorney, Agent, or Firm*—Daniel A. Monaco; Drinker Biddle & Reath LLP

(57) ABSTRACT

A process is provided for preparing an iron sucrose complex, substantially free of excipients, for providing an iron sucrose complex co-precipitated with sucrose, and for providing iron sucrose complexes in aqueous solution.

13 Claims, 6 Drawing Sheets

IRON SUCROSE COMPLEXES AND METHOD OF MANUFACTURE THEREOF

CROSS-REFERENCE TO RELATED APPLICATION

This application claims the benefit of U.S. Provisional Application Ser. No. 60/553,712, filed Mar. 16, 2004, the entire disclosure of which is herein incorporated by reference.

FIELD OF THE INVENTION

The present invention relates to a process for making iron sucrose complexes.

BACKGROUND OF THE INVENTION

A. Intravenous Iron Therapy

Iron therapy is necessary to replenish total body iron stores in patients with iron deficiency anemia. Therapeutically-active iron-containing compositions comprise iron in a form capable of increasing the amount of hemoglobin in the blood. Intravenous (IV) is particularly employed for patients who cannot tolerate oral iron therapy, are unable to adequately absorb dietary iron, or who suffer hematopoietic failure.

B. Potential Side Effects of IV Iron Therapy

One iron formulation, iron dextran, has been associated with significant adverse effects. Such effects are reported in approximately 26% of patients receiving iron dextran. See, Gupta et al., *Kidney Int.*, 1999 May; 55(5):1891-8. The underlying cause of the immediate severe reactions is unclear. However, known anaphylactic reactions to dextran have implicated dextran as the cause of the severe reactions to IV iron dextran. IV iron products free of dextran are thought to decrease or avoid these severe reactions.

One product that is dextran-free is iron sucrose complex in sucrose (VENOFER®). Product safety reports for iron sucrose demonstrate a low incidence of adverse effects. One study of 77 patients receiving a total of 757 doses, reported only 4 patients experiencing adverse events related to the administration of iron sucrose. The events reported were diarrhea, abdominal pain, nausea, constipation, and a transient minty taste. Ten patients in this study had a documented history of sensitivity reactions to iron dextran that were consistent with anaphylaxis and none experienced a hypersensitivity reaction with iron sucrose. See, Charytan et al., *Am J Kidney Dis.* 2001 February; 37(2):300-7.

C. Purity of Iron Sucrose Complexes

Iron sucrose complex in sucrose generally contains contaminants including excipients, free sucrose and by-products of the synthesis of the complex which are readily detected by techniques such as gel permeation chromatography (GPC). The compendial method of analysis for Iron sucrose complex in sucrose is reported in United States Pharmacopoeia (USP 26).

A chromatographic method for separating and purifying an iron saccharidic complex product is disclosed in U.S. Patent Application Publications 2002/0076821 and 2003/0153086. An iron sucrose complex, substantially free of excipients having a molecular weight of less than about 5,000 Daltons, is also disclosed.

Small variations in molecular structure and composition can determine the difference between an active iron complex having no adverse effects, and another iron complex that may induce adverse reactions. See, "Raising the Bar for Quality Drugs", pp. 26-31, *Chemical and Engineering News*, American Chemical Society, Mar. 19, 2001, the entire disclosure of which is incorporated herein by reference. There is a reported correlation between toxicity of iron saccharate complexes and higher molecular weight and the variability of size of the complex. See, Fishbane et al., *Semin Dial.* 2000 November-December; 13(6):381-4.

A composition of iron sucrose complex comprising a narrower molecular weight distribution may yield a safer and more efficacious therapy. There exists a need for an iron sucrose complex preparative method that results in a product with narrower molecular weight distribution as compared to existing compositions.

SUMMARY OF THE INVENTION

According to one embodiment of the invention there is provided a process of preparing iron sucrose complex, substantially free of excipients, comprising the steps of:

(a) reacting ferric hydroxide and sucrose, in an aqueous reaction mixture comprising sodium ions, at a selected molar ratio of sucrose to ferric hydroxide, for a selected time interval, at a selected temperature and at a pH in the range from about 6.5 to about 13; and (b) isolating iron sucrose complex from the aqueous reaction mixture.

The selected molar ratio of sucrose to ferric hydroxide is from about 2:1 to about 50:1, preferably from about 2:1 to about 20:1, more preferably from about 5:1 to about 20:1.

The sodium ions are present in the aqueous reaction mixture in a molar ratio of sodium ions to sucrose in the range of from about 1.0:0.5 to about 1:20, preferably from about 1:1 to about 1:10; more preferably from about 1:3 to about 1:8.

The pH of the aqueous reaction mixture is in the range from about 7 to about 13, preferably from about 8 to about 12, most preferably from about 8 to about 10.

The selected temperature of the aqueous reaction mixture is a temperature in the range from about 75° C. to about 120° C., preferably in the range from about 95° C. to about 120° C. The selected time interval is in the range from about 2 minutes to about 40 hours, preferably in the range from about 2 minutes to about 300 minutes.

According to some sub-embodiments of the invention the aqueous reaction mixture comprises from about 0.2% w/w to about 8% w/w based on the weight of the reaction mixture.

The aqueous reaction mixture may be concentrated prior to the step of isolating the iron sucrose complex to reduce the volume of the reaction mixture to a volume that is preferably in the range from about 20% to about 80% of the original volume thereof, more preferably in the range from about 20% to about 70% of the original volume thereof.

According to one embodiments of the invention, the weight average molecular weight of the isolated iron sucrose complex is in the range from about 20,000 to about 400,000 Daltons, preferably, in the range from about 20,000 to about 120,000 Daltons, more preferably in the range from about 30,000 to about 60,000 Daltons. According to certain sub-embodiments of the invention, the weight average molecular weight of the prepared iron sucrose complex is about 35,000, about 40,000, about 45,000, about 50,000, about 55,000, about 60,000, about 65,000, about 70,000, about 75,000, about 80,000, about 85,000, about 90,000, about 95,000, about 100,000, about 105,000, about 110,000, about 115,000, about 130,000, about 135,000, about 140,000, about 145,000, about 150,000, about 155,000, about 160,000, about 165,000, or about 170,000 Daltons.

According to one sub-embodiment of the invention, the step of isolating the iron sucrose comprises concentrating the reaction mixture of step (b) to form a residue comprising iron sucrose complex.

According to another sub-embodiment of the invention, the step of isolating the iron sucrose complex comprises (i) forming a mixture by adding to the reaction mixture of step (b) at least one water-miscible organic solvent in an amount sufficient to precipitate iron sucrose complex; and (ii) collecting the precipitated iron sucrose complex, from the mixture formed in step (i).

According to one embodiment of step of isolating the iron sucrose complex, the step of collecting the precipitated iron sucrose complex comprises filtration of the mixture formed in step (i).

According to another embodiment of isolating the iron sucrose complex, the step of collecting the precipitated iron sucrose complex comprises centrifugation of the mixture formed in step (i).

According to another embodiment of isolating the iron sucrose complex, the step of collecting the precipitated iron sucrose complex comprises freeze drying of the mixture formed in step (i).

According to one preferred embodiment of the invention, the ferric hydroxide used to form the iron sucrose complex according to the invention is prepared by reacting at least one ferric salt, preferably, ferric chloride, ferric nitrate, or a mixture thereof, with at least one base in a reaction mixture comprising an aqueous medium.

The collected iron sucrose complex is optionally purified, such as by.

(a) dissolving the isolated iron sucrose complex in an aqueous solvent;

(b) forming a mixture by adding to the solution of iron sucrose complex at least one water-miscible organic solvent in an amount sufficient to precipitate iron sucrose complex from the solution; and (c) separating the purified iron sucrose complex from the mixture formed in step (b).

According to one embodiment of purification of the collected iron sucrose complex, the step of separating the purified precipitated iron sucrose complex comprises filtration of the mixture formed in step (b).

According to another embodiment of purification of the collected iron sucrose complex, the step of separating the purified precipitated iron sucrose complex comprises centrifugation of the mixture formed in step (b).

The purified iron sucrose complex is optionally dried.

According to another embodiment of the invention there is provided a process of preparing an aqueous solution of sucrose and iron sucrose complex, comprising the steps of:

(a) reacting ferric hydroxide and sucrose in an aqueous reaction mixture comprising sodium ions, at a selected molar ratio of sucrose to ferric hydroxide, for a selected time interval, at a selected temperature, and at a pH in the range from about 6.5 to about 13;

(b) isolating iron sucrose complex from the reaction mixture;

(c) dissolving the isolated iron sucrose complex in an aqueous solvent to form a solution;

(d) forming a mixture by adding to the solution formed in step (c) at least one water-miscible organic solvent in an amount sufficient to precipitate iron sucrose complex from the solution;

(e) collecting purified iron sucrose complex from the mixture formed in step (d); and (f) dissolving the purified iron sucrose complex, prepared in step (e), in a solution of sucrose in water, preferably in a solution of sucrose in water containing in the range from about 20% to about 40% (wt/wt) sucrose in water, more preferably in a 30% (wt/wt) solution of sucrose in water.

According to another embodiment of the invention there is provided a process of preparing a co-precipitate comprising iron sucrose complex and sucrose, the process comprising the steps of:

(a) reacting ferric hydroxide and sucrose in an aqueous reaction mixture comprising sodium ions, at a selected molar ratio of sucrose to ferric hydroxide, for a selected time interval, at a selected temperature, and at a pH in the range from about 6.5 to about 13;

(b) isolating iron sucrose complex from the reaction mixture;

(c) dissolving the isolated iron sucrose complex in an aqueous solvent to form a solution;

(d) forming a mixture by adding to the solution formed in step (c) at least one water-miscible organic solvent in an amount sufficient to precipitate iron sucrose complex from the solution;

(e) collecting the purified iron sucrose complex from the mixture formed in step (d);

(f) dissolving purified iron sucrose complex product prepared according to step (e) in an aqueous sucrose solution;

(g) forming a mixture by adding to the solution of iron sucrose complex formed in step (f) at least one water-miscible organic solvent in an amount sufficient to co-precipitate iron sucrose complex and sucrose;

(h) collecting the co-precipitate formed in step (g); and optionally (i) drying the co-precipitate.

The ratio of purified iron sucrose complex to sucrose in the aqueous sucrose solution in step (a) of the co-precipitate preparation method is from about 1:0.1 to about 1:20 by weight (wt/wt), preferably in the range of from about 1:0.5 to about 1:5 by weight (wt/wt). The concentration of the sucrose solution employed to produce the co-precipitate is preferably in the range from about 10% to about 50% weight/volume of sucrose in water.

According to another embodiment of the invention, another process of preparing a co-precipitate comprising iron sucrose complex and sucrose is provided. The process comprises the steps of:

(a) providing a reaction mixture comprising a ferric salt dissolved in an aqueous medium;

(b) adding to the reaction mixture a first base in an amount in the range from about 1 to about 2 equivalents based on the amount of ferric salt;

(c) allowing the reaction mixture to equilibrate for a time interval in the range from about 10 to about 60 minutes;

(d) forming a mixture by adding sucrose to the equilibrated reaction mixture of step (c) in a selected molar ratio to the amount of ferric salt in the reaction mixture;

(e) heating the mixture formed in step (d) to a first temperature;

(f) forming a mixture by adding to the heated mixture formed in step (e) a second base in an amount sufficient to adjust the pH of the reaction mixture to a selected pH;

(g) heating the mixture formed in step (f) at a second temperature for a selected time interval;

(h) after the selected time interval, cooling the reaction mixture to a temperature in the range of from about 20° to about 30° C.; and (i) isolating the co-precipitate from the cooled reaction mixture.

The first selected temperature is preferably in the range from about 60° to about 90° C., more preferably from about 60° to about 80° C. and the second selected temperature is in the range from about 75° to about 120° C., preferably in the range from about 95° to about 120° C. Suitable bases for use as the first and/or second selected bases include, for example, alkali metal carbonates, e.g. sodium carbonate; alkali metal bicarbonates, e.g., sodium bicarbonate; alkali metal hydroxides, e.g., sodium hydroxide; water-soluble amines, e.g., tris-hydroxymethyl-aminomethane; and mixtures thereof.

The selected molar ratio of sucrose to the ferric salt in step (d) is in the range from about 2:1 to about 50:1, preferably, in the range from about 2:1 to about 20:1.

The step of isolating the co-precipitate preferably comprises the steps of:

(a) forming a mixture by adding to the cooled reaction mixture formed in step (h) at least one water-miscible organic solvent in an amount sufficient to co-precipitate iron sucrose complex and sucrose;

(b) collecting the co-precipitate formed in step (a); and optionally (c) drying the co-precipitate.

The cooled reaction mixture of step (h) may be optionally concentrated to reduce the volume of the reaction mixture to a volume in the range preferably from about 20% to about 80% of the original step (h) reaction mixture volume, more preferably from about 20% to about 70% of the original step (h) reaction mixture volume prior to the addition of the water-miscible organic solvent;

According to another embodiment of the invention there is provided a process of preparing an aqueous solution of sucrose and iron sucrose complex, comprising the steps of:

(a) reacting ferric hydroxide and sucrose in an aqueous reaction mixture comprising sodium ions, at a selected molar ratio of sucrose to ferric hydroxide, for a selected time interval, at a selected temperature, and at a pH in the range from about 6.5 to about 13;

(b) isolating iron sucrose complex from the reaction mixture;

(c) dissolving the isolated iron sucrose complex in an aqueous solvent to form a solution;

(d) forming a mixture by adding to the solution formed in step (c) at least one water-miscible organic solvent in an amount sufficient to precipitate iron sucrose complex from the solution;

(e) collecting the purified iron sucrose complex from the mixture formed in step (d);

(f) dissolving the purified iron sucrose complex product formed in step (e) in an aqueous sucrose solution;

(g) forming a mixture by adding to the iron sucrose complex solution formed in step (f) at least one water-miscible organic solvent in an amount sufficient to co-precipitate iron sucrose complex and sucrose;

(h) collecting the co-precipitate formed in step (g); and (i) dissolving the collected co-precipitate in water.

According to another embodiment of the invention there is provided a process of preparing an aqueous solution of sucrose and iron sucrose complex, comprising the steps of:

(a) combining ferric hydroxide and sucrose, in an aqueous reaction mixture, at a selected molar ratio of sucrose to ferric hydroxide, at a selected temperature and at a pH in the range from about 7 to about 13, preferably from about 8 to about 12, more preferably from about 9.5 to about 12, most preferably from about 10.5 to about 12;

(b) maintaining the reaction mixture at the selected temperature for a time interval from about 2 to about 300 minutes; and (c) adding to the reaction mixture a selected quantity of sucrose.

The selected temperature is in the range from about 75° to about 120° C., preferably in the range from about 95° to about 120° C., and the selected molar ratio of sucrose to ferric hydroxide in step (a) is in the range from about 2:1 to about 50:1, preferably, in the range from about 2:1 to about 20:1, more preferably, in the range from about 5:1 to about 20:1.

The quantity of sucrose added in step (c) is preferably from about 1 to about 50 times the amount of ferric hydroxide used in step (a), on a mol/mol basis, more preferably from about 1 to about 20 times the amount of ferric hydroxide used in step (a), on a mol/mol basis.

The iron sucrose complexes prepared according to the process of the invention comprise from about 1 to about 60% ferric iron (wt/wt), preferably from about 1 to about 55% ferric iron (wt/wt), more preferably from about 1 to about 50% ferric iron (wt/wt). According to some preferred embodiments, the iron sucrose complex prepared according to the process of the invention comprises from about 30% to about 50% ferric iron (wt/wt), most preferably about 45% ferric iron. According to other preferred embodiments, the iron sucrose complex prepared according to the process of the invention comprises from about 2% to about 15% ferric iron (wt/wt), most preferably about 5% ferric iron (wt/wt).

According to another embodiment of the invention, a pharmaceutical composition in a solid dosage form is provided comprising a pharmaceutically acceptable carrier and an iron sucrose complex having a molecular weight in the range from about 20,000 to about 400,000 Daltons.

Preferably, the pharmaceutical composition of the invention comprises an iron sucrose complex prepared by the process according to the present invention.

DEFINITIONS

The expression, "substantially free of excipients," used to describe the product iron sucrose complex formed by the method of the invention means that the product contains about 15% (wt/wt) of excipients or less, and correspondingly contains about 85% (wt/wt) or more iron sucrose complex. Preferably the iron sucrose complex formed by the method of the invention contains about 10% (wt/wt) of excipients or less. Most preferably, the iron sucrose complex formed by the method of the invention contains about 5% (wt/wt) of excipients or less.

The term "excipients" as used herein refers to components of the product of a process of the invention that are other than iron sucrose complex. Examples include, free sucrose, water and solvents, and substances related to the synthesis process. By "substances related to the synthesis process" is meant the reagents used in the synthesis and products of degradation of either the synthesis reagents of the reaction products.

The expression "weight average molecular weight" unless otherwise indicated, is one expression of the molecular weight of a substance which comprises a distribution of molecular weights rather than a single molecular weight. The "weight average molecular weight" is calculated as a summation of the squares of the weights of a fraction of the molecular weight distribution, divided by the total weight of the molecules. The weight average molecular weight may be determined by gel permeation chromatography (GPC) using refractive index, light scattering, small angle neutron scattering (SANS), or by sedimentation velocity.

The expression "alkali metal," as employed herein refers to metals or ions of metals found in Group I of the periodic table. Preferred alkali metals are lithium, sodium and potassium.

The term "base" as employed herein refers to a chemical species that donates electrons or hydroxide ions (Arrhenius definition) or that accepts protons (Brönsted definition). Bases include strong bases, i.e., bases that are completely dissociated in aqueous solution and weak bases, i.e., bases that are only partially dissociated in aqueous solution. Examples of strong bases include sodium hydroxide and potassium hydroxide. Examples of weak bases include ammonia and alkyl amines.

The expression "water-miscible organic solvent," unless otherwise indicated, refers to an organic solvent which is soluble in water in all proportions at standard temperature and pressure. Suitable water-miscible organic solvents include, for example, methanol, ethanol, isopropanol, acetone, acetonitrile, tetrahydrofuran, dioxane, dimethyl formamide, dimethylacetamide, and N-methylpyrrolidinone.

The term "co-precipitation", used herein refers to simultaneous precipitation of more than one dissolved substance from a solution or suspension.

The expressions, "aqueous medium" and "aqueous solvent" refer, unless otherwise indicated, to a solvent or medium that is water, or a mixture of water and one or more water-miscible organic solvents.

The expression "substantially free of crystalline material" refers, unless otherwise indicated, to a material that is indistinguishable via X-ray powder diffraction from the same material present as exclusively an amorphous solid.

The expression "solid dosage form" means a solid pharmaceutical preparation in the form of, for example a tablet, capsule, pill, powder, or granule.

DETAILED DESCRIPTION OF THE INVENTION

Figure 1:
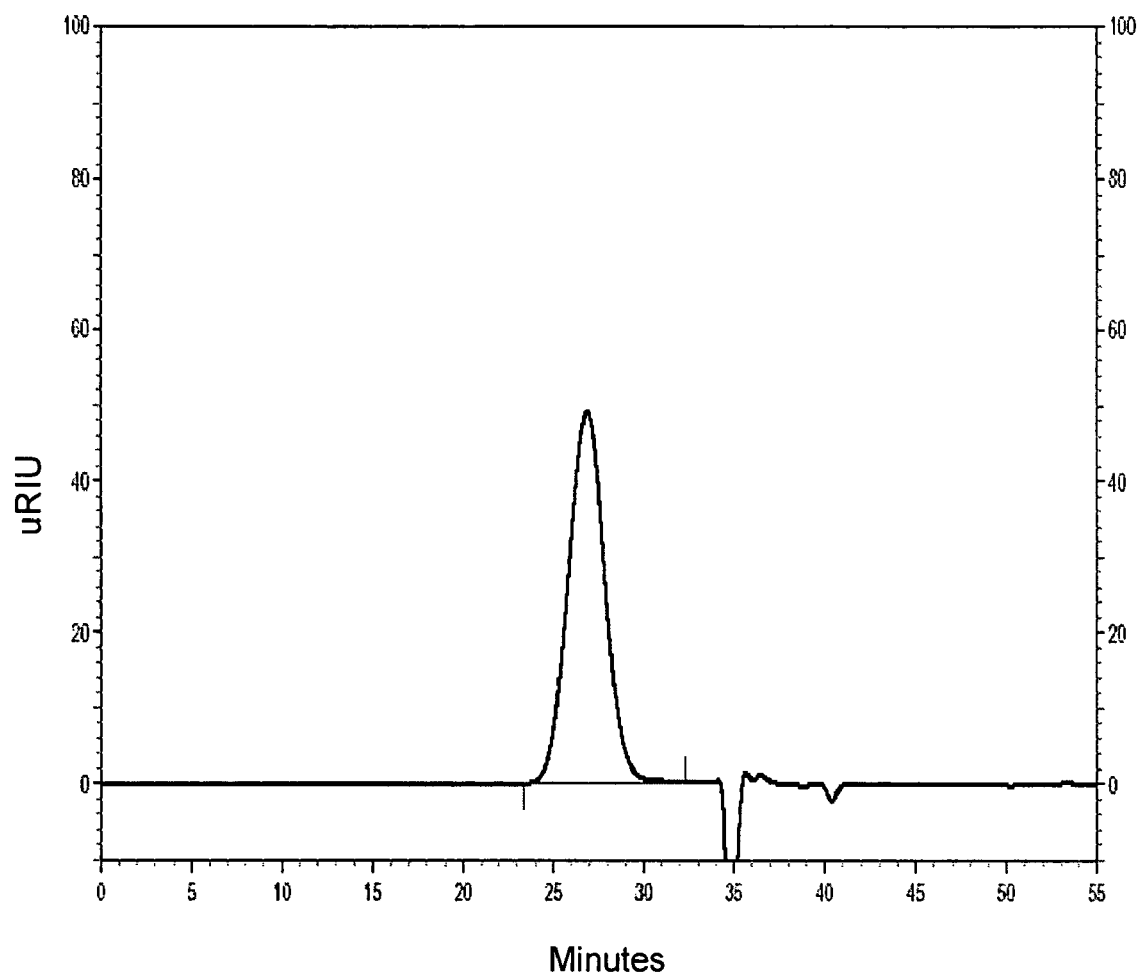
FIG. 1 shows a gel permeation chromatography (GPC) trace of iron sucrose complex prepared by the process of the invention, having a weight average molecular weight of 49,000 Daltons.

Iron sucrose complexes presently employed in therapy contain significant amounts of contaminants detectable by GPC analysis. The present invention provides a process for the preparation of iron sucrose complexes that are substantially free of excipients. The iron sucrose complexes, substantially free of excipients, can be used to formulate a therapeutic iron sucrose composition containing lower levels of contaminants.

A. Ferric Hydroxide

The term "ferric hydroxide" as employed herein, includes the various forms of ferric hydroxide, including, for example, hydrated ferric oxide, ferric oxy hydroxide, polymeric ferric hydroxide, ferric hydroxide gel, partially neutralized ferric salts and partially neutralized polymeric ferric salts. The various forms of ferric hydroxide may be expressed according to Formula I:

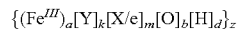

$$\{(Fe^{III})_a[Y]_k[X/e]_m[O]_b[H]_d\}_z \qquad \text{I}$$

wherein "a" and "z" represent integers that are independently 1 to about 1000, preferably 1 to about 500; "Y" is a cation other than $Fe^{III}$, for example, ammonium or alkyl ammonium; "b," "d," "k" and "m" represent integers that are independently 0 to about 1000, preferably 0 to about 500; "X" is an anion, for example, chloride, bromide, iodide, nitrate, sulfate, acetate, citrate, and other acid anions; "e" represents the equivalent number of the anion X.

B. Preparation of Ferric Hydroxide

The ferric hydroxide utilized as the starting material in the process of the present invention may be prepared by reacting a ferric salt with at least about one molar equivalent of a base, based on the amount of the ferric salt. A mixture of ferric salts, and/or a mixture of bases, may be employed. Suitable ferric salts include ferric salts wherein the anion is an anion of an acid such as, for example, chloride, bromide, iodide, nitrate, sulfate, acetate, citrate and other acid anions. Preferred ferric salts include, for example ferric chloride and ferric nitrate.

Suitable bases for reaction with the ferric salt include, for example, alkali metal carbonates, alkali metal bicarbonates, alkali metal hydroxides, water-soluble amines and mixtures thereof. Preferred bases include sodium carbonate, sodium bicarbonate, sodium hydroxide, tris-hydroxymethyl-aminoethane and mixtures thereof.

The ferric hydroxide may be prepared by (a) providing a reaction mixture comprising a ferric salt dissolved in an aqueous medium; (b) adding to the reaction mixture a first base in an amount from about 1 to about 2 equivalents based on the amount of ferric salt; (c) allowing the reaction mixture to equilibrate for a time interval greater than about 10 minutes, preferably from about 10 minutes to about 120 minutes, more preferably from about 10 minutes to about 60 minutes; (d) adding to the equilibrated reaction mixture a second base in an amount sufficient to adjust the pH of the reaction mixture to a selected pH; and (e) collecting the ferric hydroxide from the reaction mixture.

The first and second bases may be the same, or may be different bases. The bases may be added to the reaction mixture in solution or suspension in an aqueous solvent. Alternately the bases may be added neat, i.e., a base such as sodium carbonate may be added as a dry solid.

The first base may be added to the reaction mixture batchwise, i.e., all at once, or continuously or semi-continuously over a time interval at a constant or variable addition rate. A slow continuous addition may be performed as a titration wherein the pH of the mixture is continuously monitored, preferably using a pH meter. The addition of the base may be stopped when a selected pH, preferably in the range from about 2.0 to about 2.5, is achieved in the reaction mixture. The addition rate of the base for slow continuous addition is preferably from about 0.02 to about 0.2 equivalents of the base per minute, based on the amount of the ferric salt in the reaction mixture.

After the addition of the first base to the reaction mixture, the reaction mixture is allowed to equilibrate, with or without stirring. The temperature is preferably maintained in the range from about 20° to about 30° C. The pH of the reaction mixture is typically observed to drop to a pH in the range from about 1.4 to about 1.8 during the time interval when the reaction mixture is allowed to equilibrate.

The second base is preferably added to the reaction mixture continuously at a constant addition rate while the pH of the resulting mixture is monitored. Suitable addition rates are from about 0.02 to about 0.2 equivalents of the base per minute, based on the amount of the ferric salt in the reaction mixture.

The addition of the second base to the reaction mixture is continued until the pH of the reaction mixture is in the range from about 3.5 to about 9. According to some embodiments, the desired pH is about 4. According to other embodiments, the desired pH is about 7. According to still other embodiments, the desired pH is about 8.3. Ferric hydroxide forms as a precipitate in the reaction mixture during the second base addition. The ferric hydroxide precipitate begins to form at a pH of about 3.

Following complete addition of the second base, the reaction mixture, comprising a suspension of ferric hydroxide, is allowed to equilibrate for a time interval from about 5 minutes to about 60 minutes. The ferric hydroxide precipitate is observed to settle during the equilibration period.

The ferric hydroxide precipitate may be collected from the reaction mixture by any suitable method, including, for example, filtration, centrifugation, or decanting. Filtration is preferred. Suitable filtration methods include vacuum filtration, for example through a Buckner funnel. For larger scale or manufacturing operations, an agitated nutsch filter is preferred. The resulting filter cake comprising ferric hydroxide is washed with water and then prepared as a slurry in an aqueous solvent. Suitable aqueous solvents include water and mixtures of water with one or more water-miscible organic solvents, wherein the water-miscible organic solvent comprises up to about 30% of the aqueous solvent.

C. Preparation of Iron Sucrose

To prepare iron sucrose, a suspension or a slurry of ferric hydroxide, as prepared above, is reacted with sucrose in a reaction mixture comprising sodium ions. The sucrose is preferably provided as a solution of sucrose in an aqueous solvent, wherein the ratio of sucrose to aqueous solvent is preferably in the range from about 1:0.1 to about 1:4, more preferably in the range from about 1:0.2 to about 1:4. The sodium ions are preferably provided by addition of a sodium base, preferably aqueous sodium hydroxide. The mixture of the ferric hydroxide and sucrose may become basic upon the addition of the sodium base. The sodium base may be added to the aqueous medium, and the ferric hydroxide may subsequently be added. Alternately, the sodium base may be added to the mixture of the ferric hydroxide and sucrose in the aqueous medium.

The reaction mixture is optionally cooled to a temperature in the range from about 20° to about 30° C., prior to the step of isolating iron sucrose complex from the reaction mixture.

The reaction of ferric hydroxide and sucrose may be optionally monitored to determine the weight average molecular weight and purity of the iron sucrose product. Monitoring may be done by removing an aliquot of the reaction mixture and conducting a molecular weight analysis on the aliquot.

When the reaction of ferric hydroxide and sucrose is complete (as determined by observation of the clarity of the reaction mixture and by GPC analysis of reaction aliquots) the iron sucrose complex is isolated from the reaction mixture. Isolation may be achieved by adding one or more water-miscible organic solvents to the reaction mixture to precipitate the iron sucrose complex. The amount of water-miscible organic solvent added to the reaction mixture is preferably in the range of from about 0.3 to about 10 times the volume of the reaction mixture to which it is added. The product iron sucrose complex that precipitates from the reaction mixture after addition of the water-miscible organic solvent is collected from the reaction mixture. Suitable methods for collecting the product include, for example, filtration, centrifugation and decanting. The product is preferably collected by filtration. The selection of suitable filtration media, for example, a sintered glass funnel or Buckner funnel, is within the capability of one of ordinary skill in the art.

Alternately, the iron sucrose complex is isolated from the reaction mixture by concentrating the reaction mixture to form a residue comprising the iron sucrose complex. Concentration of the reaction mixture may be carried out at reduced pressure or at atmospheric pressure, utilizing concentration techniques such as, lyophilization, distillation or vacuum centrifugation. The concentration of the reaction mixture is preferably done at a temperature from about −80° to about 105° C., more preferably at a temperature from about 35° to about 105° C. Isolation of the iron sucrose complex by concentrating the reaction mixture at low temperature and low pressures is referred to herein as "freeze drying." Freeze drying may be performed using a commercially available freeze-drying apparatus by cooling the reaction mixture to below the freezing temperature, preferably from about −80° to about −50° C. and applying vacuum, preferably a pressure in the range from about 10 millitorr to about 50 torr, more preferably in the range from about 10 millitorr to about 10 torr, most preferably from about 10 millitorr to about 1 torr.

The product iron sucrose complex thus obtained, in the form of a filtrate or a residue as described above, may be optionally purified by (a) dissolving the isolated iron sucrose in an aqueous solvent; (b) forming a mixture by adding at least one water-miscible organic solvent to the solution formed in step (a), the solvent being added in an amount sufficient to precipitate iron sucrose complex from the mixture formed in step (b); and (c) collecting the precipitated purified iron sucrose complex.

The aqueous solvent used to dissolve the filtrate or residue is preferably employed in an amount in the range from about 0.2 to about 10 times the weight of the filtrate or residue to be dissolved therein, more preferably from about 0.3 to about 7 times the weight of the filtrate or residue to be dissolved therein. The pH of the resulting solution is preferably adjusted to a pH in the range from about 8 to about 14, preferably from about 9 to about 13, more preferably from about 10 to about 14, by the addition of a base such as sodium hydroxide. Suitable water-miscible organic solvents for the precipitation of purified iron sucrose complex include, for example, methanol, ethanol, acetone, tetrahydrofuran, dioxane, acetonitrile and mixtures thereof. The amount of the water-miscible organic solvent added to the solution of the residue or filtrate to precipitate iron sucrose complex is preferably in the range from a 15:1 to a 1:7 ratio of the water-miscible organic solvent to aqueous solvent (wt/wt), more preferably from a 1:0.3 to a 1:7 ratio or from a 15:1 to a 1:1 ratio (wt/wt) of the water-miscible organic solvent to aqueous solvent.

The purified iron sucrose complex thus obtained, is optionally dried. Drying of the purified iron sucrose complex may be carried out under vacuum or at atmospheric pressure, in air or under an inert atmosphere such as, for example, nitrogen. Preferably the purified product is dried at a temperature from about 25° to about 140° C.

The purified iron sucrose complex prepared according to the process of the invention preferably contains no more than about 10% wt/wt free sucrose. The purified iron sucrose complex prepared according to the process of the invention preferably no more than about 10% (wt/wt) of sodium salts such as for example, sodium chloride, sodium bromide, sodium iodide, sodium nitrate, sodium sulfate, sodium acetate or sodium citrate, or mixtures thereof.

The purified iron sucrose complex preferably contains no more than about 15% wt/wt water and solvent. The purified iron sucrose complex may exist in a hydrated form: $[Complex]_u[H_2O]_v$; wherein "Complex" is the iron sucrose complex; "u" is an integer from 1 to about 1000, preferably from 1 to about 500, and v is a rational number from about 0.2 to about 50, preferably from about 0.2 to about 25, more preferably from about 0.2 to about 10.

The thus-obtained precipitated purified iron sucrose complex, may be formulated as a parenteral iron formulation. One example of a parenteral iron formulation comprises dissolving the precipitated purified iron sucrose complex, containing from about 20% to about 50% ferric iron, in an aqueous sucrose solution, preferably about 20% aqueous sucrose, to form a parenteral iron formulation. The concentration of precipitated purified iron sucrose complex in the sucrose solution is selected such that the composition is suitable as an injectable form of ferric iron. Another example of a parenteral iron formulation comprises dissolving the precipitated purified iron sucrose complex, containing from about 2% to about 15% ferric iron, in water for injection to form a parenteral iron formulation. The concentration of precipitated purified iron sucrose complex in the aqueous solution is selected such that the composition is suitable as an injectable form of ferric iron.

According to another embodiment of the invention, there is provided a pharmaceutical composition in solid dosage form comprising a pharmaceutically acceptable carrier and an iron sucrose complex having a molecular weight in the range from about 20,000 to about 400,000 Daltons. The pharmaceutical composition of the invention may be formulated for oral administration and may be in the form of a tablet, capsule, pill, powder, granule or other suitable solid dosage form with suitable excipients and additives.

For example, the iron sucrose complex formed by the process of the present invention may be combined with at least one excipient such as a filler, binder, humectant, disintegrating agent, solution retarder, absorption accelerator, wetting agent absorbent or lubricating agent. According to one embodiment of a solid dosage form of an iron sucrose complex formed the claimed process, the active agent may be combined with carboxymethylcellulose calcium, magnesium stearate, mannitol and starch, and then formed into tablets by conventional tableting methods.

The pharmaceutical composition according the invention comprises an iron sucrose complex that contains from about 1 to about 60% ferric iron by weight, preferably from about 1 to about 50% ferric iron by weight, more preferably from about 30 to about 50% ferric iron by weight.

The pharmaceutical composition according the invention preferably contains from about 5 to about 200 mg of ferric iron, more preferably from about 10 to about 150 mg, most preferably from about 25 to about 100 mg.

The practice of the invention is illustrated by the following non-limiting examples.

EXAMPLES

The following analytical methods are employed in the Examples that follow.

Molecular Weight Determination for Iron Sucrose Complex

GPC analyses were performed using a Shimadzu Class VP, SCL10A-VP, with an LC10AD pump, equipped with a refractive index detector (Shimadzu RID 10A). The mobile phase employed was an aqueous buffer prepared by dissolving 7.12 g of dibasic sodium phosphate dihydrate, 5.52 g of monobasic sodium phosphate, and 0.40 g of sodium azide in 2 liters of water.

The separation media consists of two 7.8-mm×30-cm columns (Waters Ultrahydrogel GPC column containing packing L39, with pore sizes of 1000 A and 120 A, respectively) set up in series. The column temperatures were maintained at 45°+/−2° and the flow rate was about 0.5 mL per minute.

Standard solutions (Waters Dextran molecular weight standard kit part # WAT 054392) were prepared by accurately weighing about 20 mg of each polysaccharide molecular weight standard (5,000-400,000 Da) into separate 5-mL volumetric flasks. Mobile phase (about 4 mL) was added to each flask and the resulting mixture was allowed to stand at or below 25° C. for a minimum of 12 hours. After the agglomerate particles of each standard solution swelled to their fullest extent, each standard solution was gently agitated until the polysaccharide dissolved. Chromatograms of freshly prepared standard solutions regularly show a small, unidentified secondary peak following the main peak. Any standard solutions wherein the secondary peak reached half the height of the main peak were discarded.

A system suitability test solution was also prepared by dissolving 200 mg of high molecular weight dextran and 100 mg of glucose in 20 mL of the mobile phase.

Test sample solutions of iron sucrose complex for analysis were prepared by transferring about 250 mg of each iron sucrose complex to a 10-mL volumetric flask, diluting to the line with mobile phase, and mixing. Test samples which were reaction aliquots were prepared by diluting 1 mL of the reaction mixture to 10 mL with mobile phase.

About 25 μL of each standard solution and test sample solution was injected (Shimadzu auto injector SIL10 A-VP) onto the column. Chromatograms were recorded and the retention times and peak areas of all components above the detectability threshold were measured. The analyte retention times were as follows:

| Iron sucrose complex peak | About 27 minutes |
| Sucrose (free) peak | About 38 minutes |

The retention times of the standard solutions and their molecular weights were plotted to generate a third order (cubic) calibration curve. The correlation coefficient obtained was not less than 0.98. The molecular weight of the complex was calculated using the calibration curve. The molecular weight distribution curve of the each sample was sliced into fractions. The weight-average molecular weight (Mw) was calculated according to the formula:

$$\Sigma(A_T M_T)/\Sigma A_T$$

wherein $A_T$ is the area of each fraction of the sample distribution; and $M_T$ is the corresponding mean molecular weight of each fraction as determined from its retention time on the calibration curve. The molecular weight distribution curve obtained for the Injection conformed to the following parameters:

Mw=34,000-60,000 Da,
Mn=not less than 24,000 Da, and
Mw/Mn=not more than 1.7.

FTIR Analyses of Iron Sucrose Complex:

About 50 mg of iron sucrose complex was finely crushed using an agate pestle and mortar. The crushed sample was placed over the trough plate of the Horizontal Attenuated Total Reflectance (HATR) assembly of a Perkin Elmer Spectrum 1 FTIR Spectrometer. The spectrum was recorded (4 scans, 4000 to 800 cm$^{-1}$) and corrected for background signal.

NMR Analyses of Iron Sucrose Complex:

About 5 mg of iron sucrose complex was dissolved in 1.5 mL of $D_2O$ and transferred into an NMR sample tube. The proton NMR was recorded (−5 to 20 ppm, Varian 400 MHz NMR spectrometer) using standard parameters with 3-trimethylsilylpropionic acid sodium salt (TSP) as an internal standard.

Determination of Iron Content by Atomic Absorption Spectroscopy (AAS)

An iron content calibration curve was prepared by plotting absorbances at the iron emission line at 248.3 nm versus concentration (μg per mL) for a series of standard iron solutions. The absorbances were measured with a Perkin Elmer 5000 atomic absorption spectrophotometer equipped with an iron hollow-cathode lamp and air-acetylene flame, and using a calcium chloride solution as a blank. Reaction aliquots from reactions performed in the preparation of the iron sucrose complexes of the invention were dissolved in water, and the absorbance at 248.3 nm were recorded. The content of iron in the samples prepared from reaction aliquots was determined according to the prepared calibration curve.

Elemental Analyses

Elemental analyses (carbon and hydrogen) were performed by Atlantic MicroLabs, Norcross, Ga.

Determination of Degree of Crystallinity of Iron Sucrose Complexes by X-ray Powder Diffraction Analyses X-ray powder diffraction analyses were performed on the dried purified products of the reactions performed in the preparation of the iron sucrose complexes of the invention. Each sample of iron sucrose complex of the invention was analyzed as a fine powder. The dried purified reaction products required no additional processing before X-ray diffraction analysis. The powder sample to be analyzed was placed onto a zero background holder and inserted into a Philips PW1800 XR diffractometer. The X-ray analysis comprised Cu radiation over the angular range (theta) of 5° to 60° with a step size of 0.03°. The analyses at each step required from about 5 to about 30 seconds depending on the degree of crystallinity of the sample.

Example 1

Preparation of Iron Sucrose Complex

Step 1—Preparation of Ferric Hydroxide

Ferric chloride hexahydrate (5 g, 18.5 mmol) was dissolved in deionized water (20 mL) at a temperature of about 20° C. To the stirred ferric chloride solution was added sodium carbonate 30% w/v aqueous solution dropwise with the pH of the ferric chloride solution monitored during the addition (first base addition). The addition was stopped when the pH reached 2.2. The pH of the mixture was monitored using a pH meter. The temperature of the mixture was maintained at about 20° C. Following the addition of sodium carbonate, the resulting mixture was dark brown to reddish brown in color. The mixture was allowed to stand for about 30 min., during which time the pH of the reaction mixture was observed to drop to 1.7. Additional sodium carbonate solution (second base addition) was added as the pH of the mixture was monitored. A gelatinous precipitate appeared at a pH of about 3.0. The addition of the sodium carbonate solution was continued until the pH of the mixture reached 4.0, yielding a suspension of ferric hydroxide. Following the addition of sodium carbonate solution, the reaction mixture was allowed to stand for about 10 minutes to allow the precipitate to settle. The precipitated ferric hydroxide was then collected by filtration and washed with water (25 mL). The wet filter cake (about 15 g) was made into a slurry in water (about 20 mL).

Step 2—Preparation of the Iron Sucrose Complex

To a 100 mL three necked round bottom flask, fitted with reflux condenser and stirrer assembly, was added water (15 mL) and sucrose (30 g). The resulting mixture was heated in an oil bath maintained at 120° C. for about 10 min. The temperature of the mixture reached about 100-105° C. Sodium hydroxide (about 2 mL, 20% w/v) was added to the heated reaction mixture. Then the slurry of ferric hydroxide prepared in Step 1 was added to the sucrose mixture over about 15 min. The reaction mixture formed a clear dark brown solution after the addition of the suspension of ferric hydroxide was completed. Following the addition of the ferric hydroxide slurry, the temperature of the reaction mixture was maintained at about 100 to 105° C. for about 2 hrs. The reaction mixture was subsequently cooled to ambient temperature (20 to 25° C.). An aliquot (1 mL) of the reaction mixture was removed for GPC analysis to confirm the weight average molecular weight of the product iron sucrose complex (about 55,000 Daltons).

Step 3—Isolation of the Iron Sucrose Complex

Figure 3:
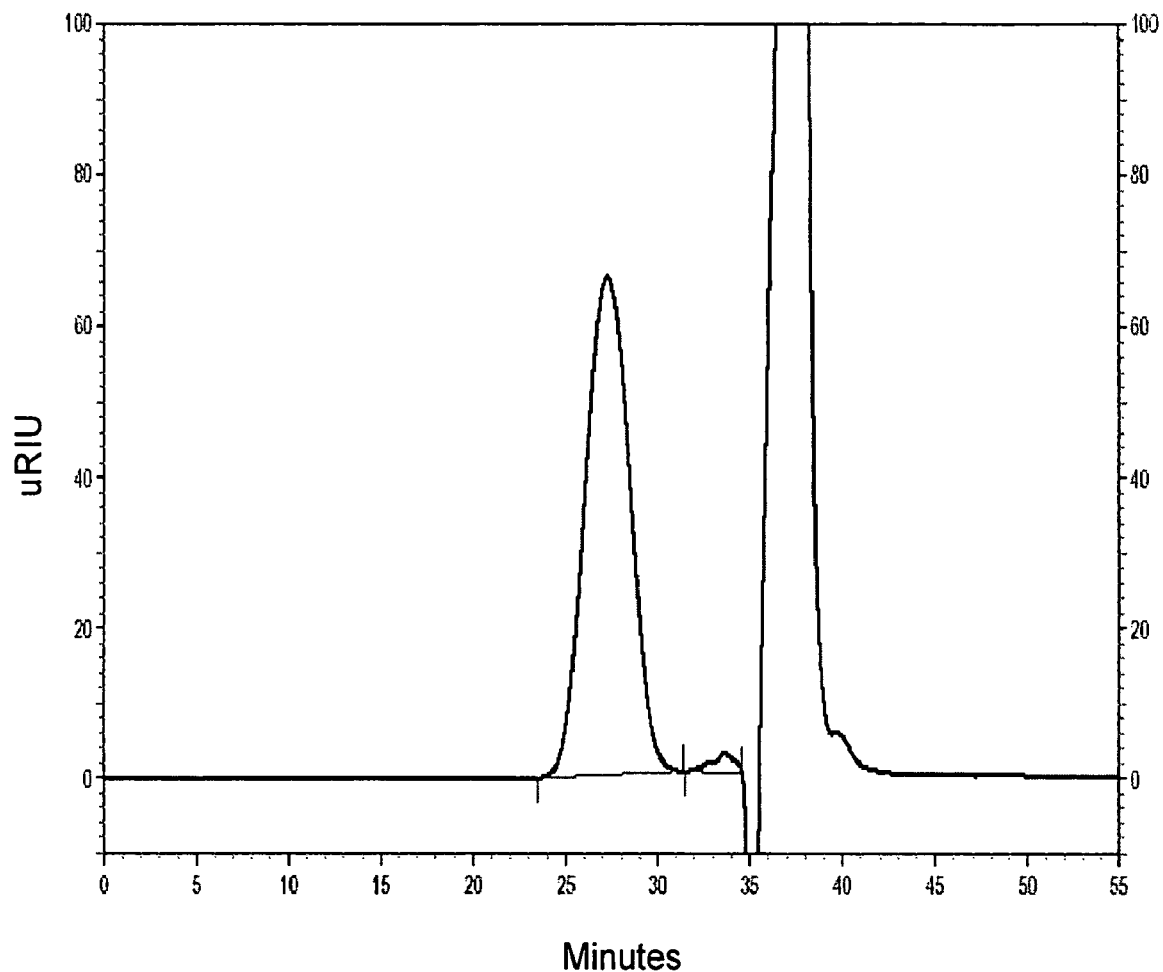
FIG. 3 shows a GPC trace of VENOFER® brand iron sucrose complex in sucrose wherein the iron sucrose complex has a weight average molecular weight of 46,000 Daltons.

A water-miscible organic solvent (ethanol, about 350 mL) was added to the reaction mixture formed in Step 2, at about 25° C. with stirring. A dark brown precipitate formed and was collected by filtration. The collected product was further purified by dissolving it in water (10 mL) and subsequently adding ethanol (50 mL) to the dissolved product to precipitate a purified product. The precipitate was collected by filtration, washed with ethanol, and dried under vacuum at about 50° C. The purified product was identified as iron sucrose complex and was analyzed by GPC. The GPC analysis showed that the complex corresponding to the principle peak was present in greater than 95% purity and that the weight average molecular weight remained at about 55,000 Daltons. This peak corresponds to the iron sucrose peak obtained on analysis of the marketed iron sucrose in sucrose (VENOFER®), shown in FIG. 3. The molecular weight and weight average molecular weight values were determined using calibration curves and third order fitting. The procedure for molecular weight determination of iron sucrose was the same as that which is described in USP 26, page 1016. The content of Fe, C and H were determined for the precipitated Iron sucrose complex: Fe, 47%; C, 25%; H, 7%;

Example 2

Preparation of Iron Sucrose Complex

The procedure of Example 1 was followed, except that the ferric salt used in Step 1 was ferric nitrate nonahydrate (7.5 g, 18.5 mmol).

The GPC analyses of the reaction aliquot and of the final purified and dried product indicated that the complex corresponding to the principle peak was present in greater than 95% purity and that the weight average molecular weight was about 45,000 Daltons.

Example 3

Preparation of Iron Sucrose Complex

The procedure of Example 1 was followed, except that the second base addition was continued until the pH reached 7.0.

The GPC analyses of the reaction aliquot and of the final purified and dried product indicated that the complex corresponding to the principle peak was present in greater than 95% purity and that the weight average molecular weight was about 65,000 Daltons.

Example 4

Preparation of Iron Sucrose Complex

The procedure of Example 1 was followed, except that the second base addition was continued until the pH reached 8.3.

Figure 4:
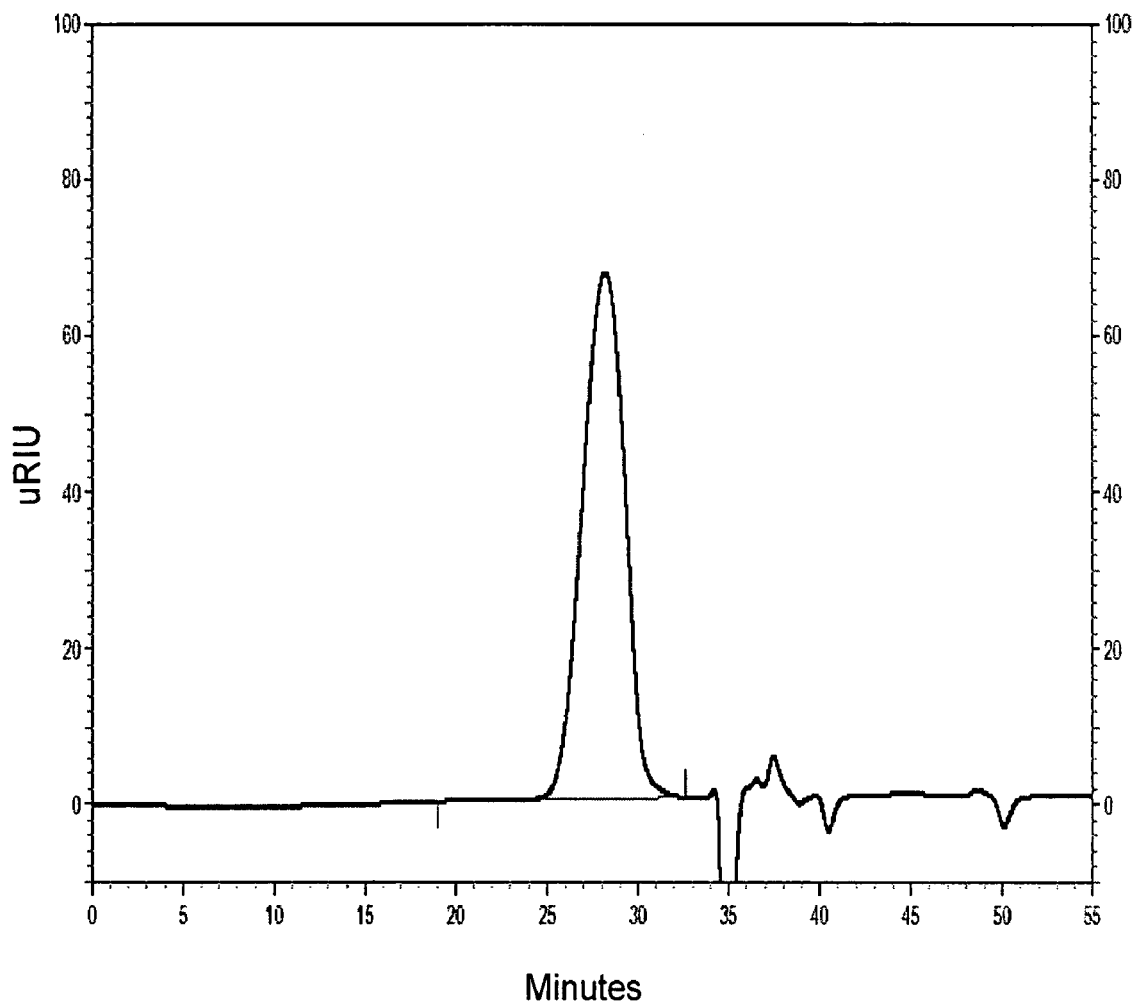
FIG. 4 shows a GPC trace of iron sucrose complex wherein the iron sucrose complex has a weight average molecular weight of 90,000 Daltons.

The GPC analyses of the reaction aliquot and of the final purified and dried product indicated that the complex corresponding to the principle peak was present in greater than 95% purity and that the weight average molecular weight was about 90,000 Daltons (FIG. 4).

Example 5

Preparation of Iron Sucrose Complex

The procedure of Example 1 was followed, except that in step 2, the 20% sodium hydroxide solution (2 mL) was added after the completion of the addition of the slurry of ferric hydroxide, and in Step 3, the water miscible solvent was methanol.

The GPC analyses of the reaction aliquot and of the final purified and dried product indicated that the complex corresponding to the principle peak was present in greater than 95% purity and that the weight average molecular weight was about 120,000 Daltons.

Example 6

Preparation of Iron Sucrose Complex

The procedure of Example 1 was followed, except that the first base addition comprised addition of the base (sodium carbonate 30% w/v aqueous solution) as a single portion of 3.3 mL (about 1 equivalent based on the amount of ferric salt).

The GPC analyses of the reaction aliquot and of the final purified and dried product indicated that the complex corresponding to the principle peak was present in greater than 95% purity and that the weight average molecular weight was about 50,000 Daltons. The GPC analysis of the purified product is shown in FIG. 1. This peak corresponds to the iron sucrose peak obtained on analysis of the marketed iron sucrose in sucrose (VENOFER®), shown in FIG. 3.

Figure 5:
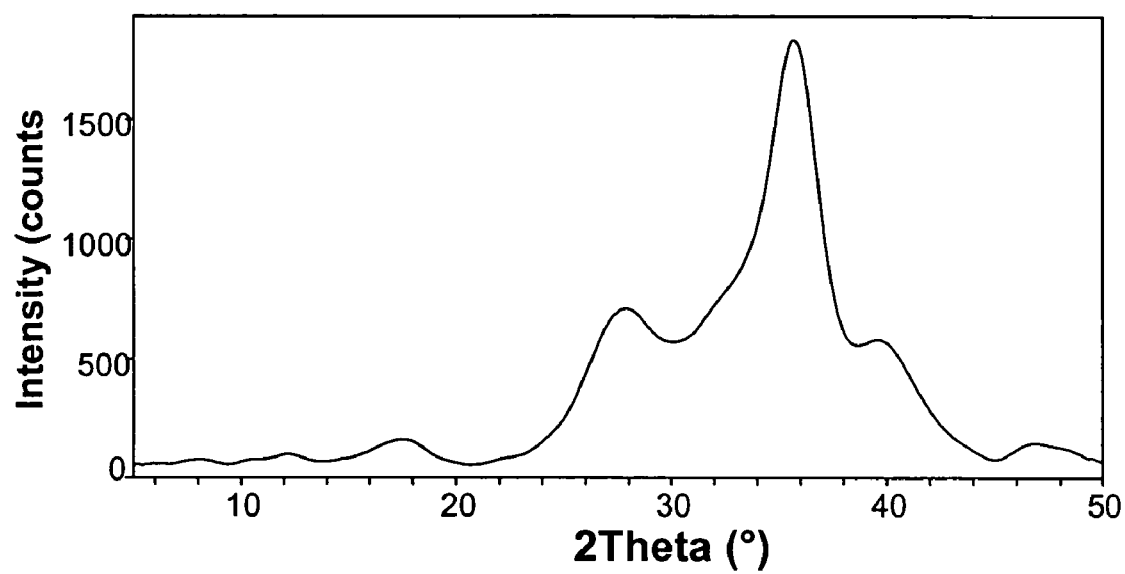
FIG. 5 shows an X-ray diffractogram of a dried, purified iron sucrose complex prepared in Example 6 which is amorphous and substantially free of crystalline sucrose.

Powder diffraction analysis was obtained for a sample of the dried purified product. The powder diffraction analysis is reproduced in FIG. 5. The powder diffraction analysis indicates the presence of an amorphous product which is substantially free of crystalline sucrose.

Example 7

Preparation of Iron Sucrose Complex

The procedure of Example 1 was followed, except that the first base addition comprised batchwise addition of the base (sodium carbonate 30% w/v aqueous solution) in a single portion of 6.6 mL (about 2 equivalents based on the amount of ferric salt).

The GPC analyses of the reaction aliquot and of the final purified and dried product indicated that the complex corresponding to the principle peak was present in greater than 95% purity and that the weight average molecular weight was about 45,000 Daltons.

Example 8

Preparation of Iron Sucrose Complex

Step 1—Preparation of Ferric Hydroxide

Step-1 of the procedure of Example 1 was followed except that the first base addition comprised batchwise addition of the base (sodium carbonate 25% w/v aqueous solution) in a single portion of 6.6 mL (about 2 equivalents based on the amount of ferric salt).

Step 2—Preparation of the Iron Sucrose Complex

Step-2 of the procedure of Example 1 was followed.

Step 3—Isolation of Iron Sucrose Complex

The reaction mixture formed in Step 2 was concentrated by distillation for about 30 minutes at about 105° C. with stirring to form a residue. The purified product was precipitated from the residue by the addition of ethanol (50 mL). The precipitate was collected by filtration, washed with ethanol, and dried under vacuum at about 50° C. The purified product was identified by GPC as iron sucrose complex. The GPC analysis showed a molecular weight corresponding to the iron sucrose complex peak at about 45,000 Daltons and an additional peak for sucrose.

Figure 6:
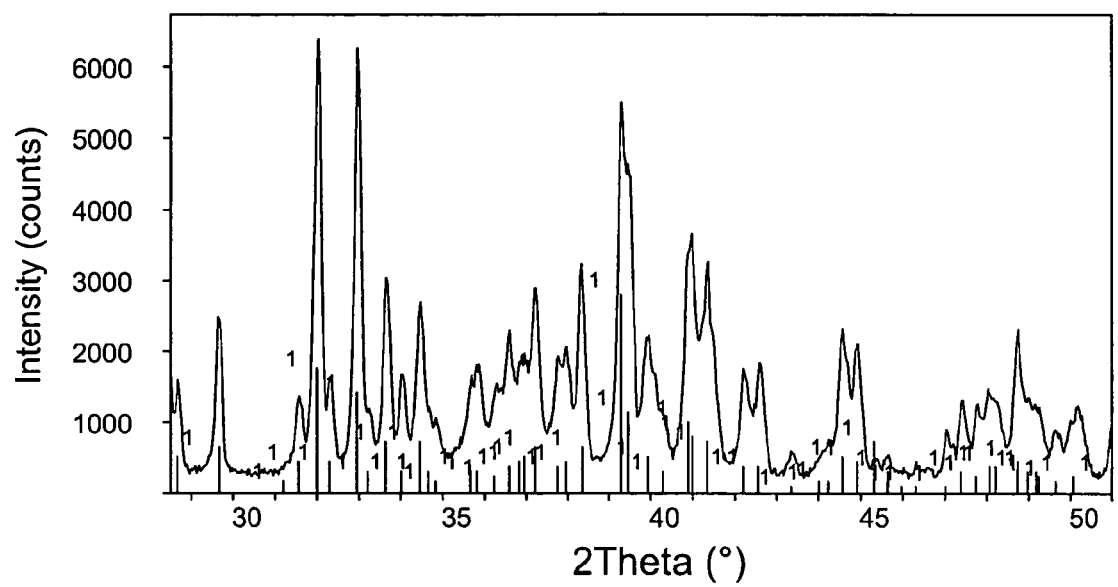
FIG. 6 shows an X-ray diffractogram of a dried, purified iron sucrose complex prepared in Example 8 which contains detectable amount of crystalline sucrose.

Powder diffraction analysis was obtained for a sample of the dried purified product. The powder diffraction analysis is reproduced in FIG. 6. The powder diffraction analysis indicates product which contains a significant amount of crystalline iron sucrose complex.

Example 9

Preparation of Iron Sucrose Complex

The procedure of Example 7 was followed, except that the second base addition was continued until the pH reached 7.0.

The GPC analyses of the reaction aliquot and of the final purified and dried product indicated that the complex corresponding to the principle peak was present in greater than 95% purity and that the weight average molecular weight was about 60,000 Daltons.

Example 10

Preparation of Iron Sucrose Complex and Analysis of Variation in Weight Average Molecular Weight Over Time The procedure of Example 9 was followed, except for the following changes in Steps 1 and 2.

Step 1: The amount of the first base addition was 3.3 mL of 30% wt/Vol, aqueous sodium carbonate.

Step 2: One aliquot of the reaction mixture was removed immediately following completion of the addition of the ferric hydroxide slurry. The reaction mixture was then maintained at 100-105° C. for about two hours, and then cooled to ambient temperature (20 to 25° C.). A second aliquot of the reaction mixture was removed. GPC analysis was performed on both the first and second aliquots. The weight average molecular weight determined for the first aliquot was about 85,000 Daltons. The weight average molecular weight determined for the second aliquot was about 50,000 Daltons.

The GPC analyses of the final purified and dried product indicated a weight average molecular weight of about 50,000 Daltons. This peak corresponds to the iron sucrose peak obtained on analysis of the marketed iron sucrose in sucrose (VENOFER®), shown in FIG. 3.

Example 11

Preparation of Iron Sucrose Complex

The procedure of Example 9 was followed, except for the following changes in Steps 1 and 2.

Step 1: The amount of the first base addition was 3.3 mL of 30% wt/Vol, aqueous sodium carbonate.

Step 2: The water-miscible organic solvent used to precipitate the complex was methanol (350 mL), and the water-miscible organic solvent used to precipitate the purified complex was methanol (50 mL).

The GPC analyses of the reaction aliquot and of the final purified and dried product indicated that the complex corresponding to the principle peak was present in greater than 95% purity and that the weight average molecular weight was about 50,000 Daltons. This peak corresponds to the iron sucrose peak obtained on analysis of the marketed iron sucrose in sucrose (VENOFER®), shown in FIG. 3.

Example 12

Preparation of Iron Sucrose Complex

The procedure off Example 9 was followed except the amount of the first base addition in Step 1 was 3.3 mL of 30% wt./Vol, aqueous sodium carbonate, the water-miscible organic solvent used to precipitate the complex in Step 2 was isopropanol (350 mL), and the water-miscible organic solvent used to precipitate the purified complex in Step 2 was isopropanol (50 mL).

The GPC analyses of the reaction aliquot and of the final purified and dried product indicated that the complex corresponding to the principle peak was present in greater than 95% purity and that the weight average molecular weight was about 50,000 Daltons. This peak corresponds to the iron sucrose peak obtained on analysis of the marketed iron sucrose in sucrose (VENOFER®), shown in FIG. 3.

Example 13

Preparation of Iron Sucrose Complex

The procedure of Example 9 was followed, except the amount of the first base addition in Step 1 was 3.3 mL of 30% wt./Vol, aqueous sodium carbonate, the water-miscible organic solvent used to precipitate the complex in Step 2 was acetone (350 mL), and the water-miscible organic solvent used to precipitate the purified complex in Step 2 was acetone (50 mL).

The GPC analyses of the reaction aliquot and of the final purified and dried product indicated that the complex corresponding to the principle peak was present in greater than 95% purity and that the weight average molecular weight was about 50,000 Daltons. This peak corresponds to the iron sucrose peak obtained on analysis of the marketed iron sucrose in sucrose (VENOFER®), shown in FIG. 3.

Example 14

Preparation of Iron Sucrose Complex

The procedure of Example 9, except the amount of the first base addition in Step 1 was 3.3 mL of 30% wt/Vol, aqueous sodium carbonate, the water-miscible organic solvent used to precipitate the complex in Step 2 was acetonitrile (350 mL), and the water-miscible organic solvent used to precipitate the purified complex in Step 2 was acetonitrile (50 mL).

The GPC analyses of the reaction aliquot of Step 2 and of the final purified and dried product indicated that the complex corresponding to the principle peak was present in greater than 95% purity and that the weight average molecular weight was about 50,000 Daltons. This peak corresponds to the iron sucrose peak obtained on analysis of the marketed iron sucrose in sucrose (VENOFER®), shown in FIG. 3.

Example 15

Preparation of Iron Sucrose Complex

The procedure of Example 9 was followed, except the amount of the first base addition in Step 1 was 3.3 mL of 30% wt/Vol, aqueous sodium carbonate, and the purified product was dried under vacuum at a temperature of 120° C. Also, the water-miscible organic solvent used to precipitate the complex and to precipitate the purified complex in Step 2 was acetonitrile (350 mL and 50 mL, respectively).

The GPC analyses of the reaction aliquot of Step 2 and of the final purified and dried product indicated that the complex corresponding to the principle peak was present in greater than 95% purity and that the weight average molecular weight was about 50,000 Daltons. This peak corresponds to the iron sucrose peak obtained on analysis of the marketed iron sucrose in sucrose (VENOFER®), shown in FIG. 3.

Example 16

Preparation of Iron Sucrose Complex

The procedure of Example 9 was followed, except the amount of the first base addition in Step 1 was 3.3 mL of 30% wt/Vol, aqueous sodium carbonate, and the amount of sucrose used in step 2 was 15 g. Also, the water-miscible organic solvent used to precipitate the complex and to precipitate the purified complex in Step 2 was acetonitrile (350 mL and 50 mL, respectively).

The GPC analyses of the reaction aliquot of Step 2 and of the final purified and dried product indicated that the complex corresponding to the principle peak was present in greater than 95% purity and that the weight average molecular weight was about 75,000 Daltons.

Example 17

Preparation of Iron Sucrose Complex

The procedure of Example 9 was followed, except the first base addition in Step 1 was the addition of 1 g of sodium carbonate added as a solid. Also, the water-miscible organic solvent used to precipitate the complex and to precipitate the purified complex in Step 2 was acetonitrile (350 mL and 50 mL, respectively).

The GPC analyses of the reaction aliquot of Step 2 and of the final purified and dried product indicated that the complex corresponding to the principle peak was present in greater than 95% purity and that the weight average molecular weight was about 55,000 Daltons.

Example 18

Preparation of Iron Sucrose Complex

The procedure of Example 9 was followed, except the first base addition in Step 1 was solid sodium bicarbonate (first addition was 1.6 g added all at once). Also, the water-miscible organic solvent used to precipitate the complex and to precipitate the purified complex in Step 2 was acetonitrile (350 mL and 50 mL, respectively).

The GPC analyses of the reaction aliquot of Step 2 and of the final purified and dried product indicated that the complex corresponding to the principle peak was present in greater than 95% purity and that the weight average molecular weight was about 55,000 Daltons. This peak corresponds to the iron sucrose peak obtained on analysis of the marketed iron sucrose in sucrose (VENOFER®), shown in FIG. 3.

Example 19

Preparation of Iron Sucrose Complex

The procedure of Example 9 was followed, except the first added base in Step 1 was solid sodium bicarbonate (first addition was 1.6 g added all at once), and the second added base was sodium hydroxide (20% aqueous solution). Also, the water-miscible organic solvent used to precipitate the complex and to precipitate the purified complex in Step 2 was acetonitrile (350 mL and 50 mL, respectively).

The GPC analyses of the reaction aliquot of Step 2 and of the final purified and dried product indicated that the complex corresponding to the principle peak was present in greater than 95% purity and that the weight average molecular weight was about 80,000 Daltons.

Example 20

Preparation of Iron Sucrose Complex

The procedure of Example 9 was followed, except that the first added base in Step 1 was tris-hydroxyethylaminomethane (first addition is 2.2 g added all at once), and the second added base was sodium hydroxide (20% aqueous solution). Also, the water-miscible organic solvent used to precipitate the complex and to precipitate the purified complex in Step 2 was acetonitrile (350 mL and 50 mL, respectively).

The GPC analyses of the reaction aliquot of Step 2 and of the final purified and dried product indicated that the complex corresponding to the principle peak was present in greater than 95% purity and that the weight average molecular weight was about 160,000 Daltons.

Example 21

Preparation of Iron Sucrose Complex

The procedure of Example 9 was followed, except the amount of the first base addition in Step 1 was 3.3 mL of 30% wt/Vol, aqueous sodium carbonate, and in Step 2 the heating temperature was 80° C. and the heating time was about 4 hours.

The GPC analyses of the reaction aliquot of Step 2 and of the final purified and dried product indicated that the complex corresponding to the principle peak was present in greater than 95% purity and that the weight average molecular weight was about 80,000 Daltons.

Example 22

Preparation of Iron Sucrose Complex

The procedure of Example 9 was followed, except the amount of the first base addition in Step 1 was 3.3 mL of 30% wt/Vol, aqueous sodium carbonate. Also, in Step 2, the solvent was 5 mL of water and 5 mL of ethanol, the reaction temperature was about 80° C., and the heating time was about 4 hours.

The GPC analyses of the reaction aliquot of Step 2 and of the final purified and dried product indicated that the complex corresponding to the principle peak was present in greater than 95% purity and that the weight average molecular weight was about 90,000 Daltons.

Example 23

Preparation of Iron Sucrose Complex

The procedure of Example 9 was followed, except the amount of the first base addition in Step 1 was 3.3 mL of 30% wt/Vol, aqueous sodium carbonate.

In Step 2, the GPC analysis of the aliquot showed a weight average molecular weight of the product was about 50,000 Daltons.

Also in Step 3, the reaction mixture was concentrated by vacuum distillation at 35° C., prior to the addition of ethanol (50 mL) which served to precipitate the iron sucrose complex. In addition, the purification of Step 3 was carried out by dissolving the product in a 40% wt/Vol. sucrose solution in water (10 mL) and subsequently adding ethanol (50 mL) to the dissolved product to precipitate a purified product. The precipitate was collected by filtration, washed with ethanol, and dried under vacuum at about 50° C.

Figure 2:
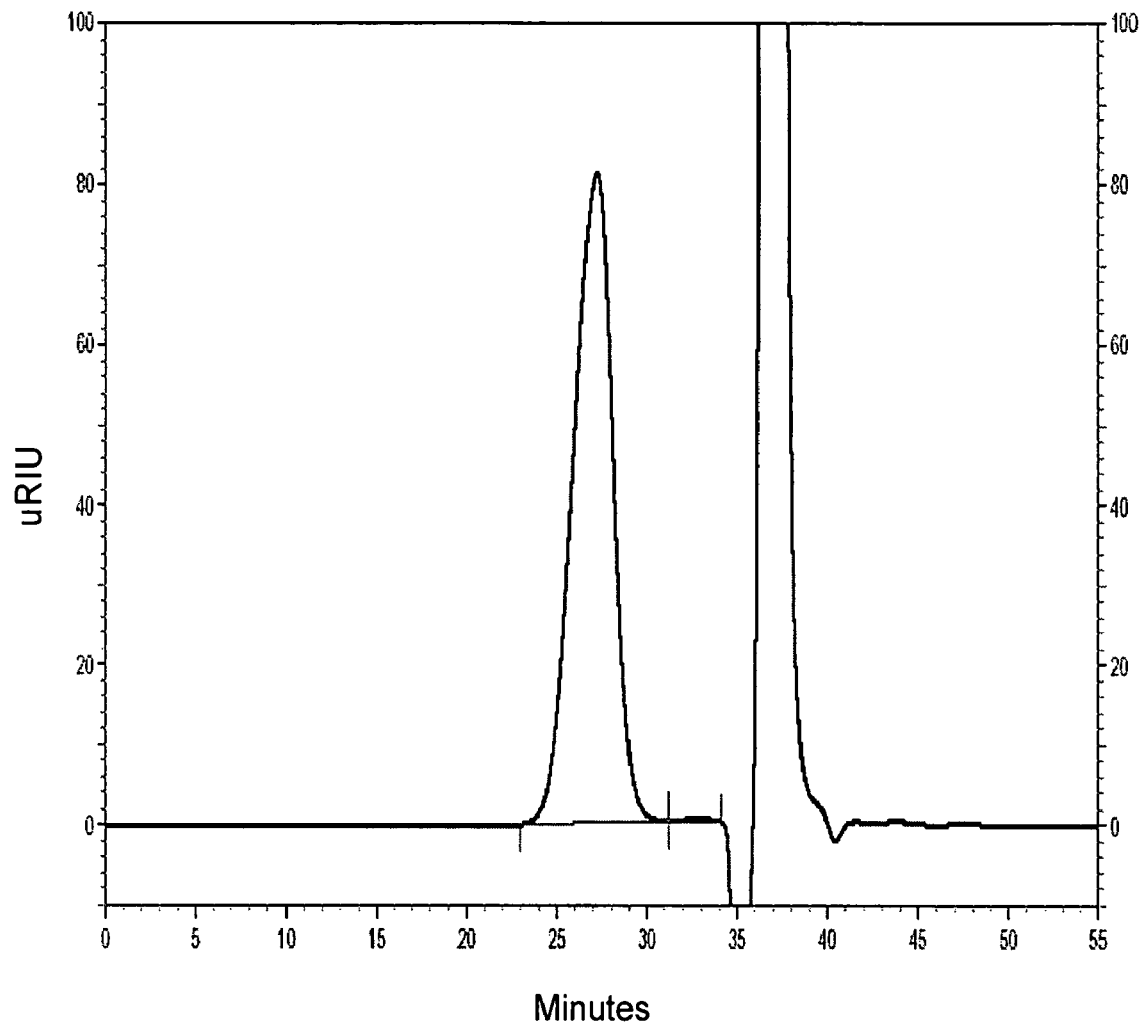
FIG. 2 shows a GPC trace of iron sucrose complex in 20% aqueous solution, prepared by the process of the invention, wherein the iron sucrose complex has a weight average molecular weight of 50,000 Daltons.

The purified product was identified as iron sucrose complex co-precipitated with sucrose and was analyzed by GPC. The GPC analysis, shown in FIG. 2, showed that the weight average molecular weight of the product was about 50,000 Daltons. This peak corresponds to the iron sucrose peak obtained on analysis of the marketed iron sucrose in sucrose (VENOFER®), shown in FIG. 3.

Example 24

Preparation of Iron Sucrose Complex

The procedure of Example 9 was followed, except the amount of the first base addition in Step 1 was 3.3 mL of 30% wt/Vol, aqueous sodium carbonate.

In Step 2, the GPC analysis of the aliquot showed a weight average molecular weight of the product was about 50,000 Daltons.

Also in Step 3, the reaction mixture was concentrated by vacuum distillation at 35° C. prior to the addition of ethanol (50 mL) which served to precipitate the iron sucrose complex. In addition, the purification of Step 3 was carried out by dissolving the product in a 20% wt/Vol. sodium chloride solution in water (10 mL) and subsequently adding ethanol (50 mL) to the dissolved product to precipitate a purified product. The precipitate was collected by filtration, washed with ethanol, and dried under vacuum at about 50° C.

The purified product was identified as iron sucrose complex co-precipitated with sodium chloride confirmed by the test for chloride ions using silver nitrate. The product was also analyzed by GPC.

Example 25

Preparation of Iron Sucrose Complex

The procedure of Example 9 was followed, except the amount of the first base addition in Step 1 was 3.3 mL of 30% wt/Vol, aqueous sodium carbonate, and the ferric salt employed in Step 1 consisted of a combination of ferric chloride hexahydrate (2.5 g, 9.25 mmol) and ferric nitrate nonahydrate (3.75 g, 9.25 mmol).

Also in Step 3, the reaction mixture was concentrated by vacuum distillation at 35° C. prior to the addition of ethanol (50 mL) which served to precipitate the iron sucrose complex.

The GPC analyses of the reaction aliquot and of the final purified and dried product indicated that the complex corresponding to the principle peak was present in greater than 95% purity and that the weight average molecular weight was about 50,000 Daltons. This peak corresponds to the iron sucrose peak obtained on analysis of the marketed iron sucrose in sucrose (VENOFER®), shown in FIG. 3.

Example 26

Isolation of Iron Sucrose Complex Via Concentration of the Reaction Mixture According to Step 2 of Example 6

The procedure of Example 6 was followed, except the reaction mixture of Step 2 was subjected to vacuum distillation at 50 to 60° C. to reduce the volume of the reaction mixture to about 30% of its original volume. The temperature of the resulting mixture was adjusted to 25° C., and ethanol (50 mL) was added with stirring. A dark brown precipitate formed. The precipitate was collected by filtration. The collected product was purified by dissolution in water (10 mL). Addition of ethanol (50 mL) to the dissolved product served to form a precipitate. This precipitate was collected by filtration, washed with ethanol and dried under vacuum at about 50° C. The product was identified as iron sucrose complex co-precipitated with sucrose. Analysis (GPC) of the purified product, and of the aliquot removed in Step 2, yielded a weight average molecular weight for the peak corresponding to the iron sucrose complex of about 70000 Daltons.

Example 27

Preparation (18 mmol Scale) of Iron Sucrose Complex without Isolating Ferric Hydroxide by Filtration Step 1—Preparation of Ferric Hydroxide Ferric chloride hexahydrate (5 g) was dissolved in deionized water (20 mL) at a temperature of about 20° C. To the stirred ferric chloride solution was added sodium carbonate (3.3 mL of 30% w/v aqueous solution). The pH of the mixture was monitored using a pH meter. The temperature of the mixture was maintained at about 20° C. Following the addition of sodium carbonate, the resulting mixture was dark brown to reddish brown in color. The mixture was allowed to stand for about 30 min., during which time the pH of the reaction mixture was observed to drop to 1.7.

Step 2—Preparation of the Iron Sucrose Complex

To the above-prepared suspension of ferric hydroxide at a pH of 1.7, was added sucrose (30 g). The resulting mixture was heated to a temperature of about 80° C. Sodium carbonate was added to adjust the pH to 7.0. The resulting mixture was heated to a temperature of 100° C. and stirred at 100° C. for about 15 minutes. Sodium hydroxide (about 3 mL, 20% w/v) was added to the heated reaction mixture. The reaction mixture formed a clear dark brown solution after the addition of the suspension of ferric hydroxide was completed. Following the addition of the sodium hydroxide solution, the temperature of the reaction mixture was maintained at about 100 to 105° C. for about 3 hrs. The reaction mixture was subsequently cooled to ambient temperature (20 to 25° C.). An aliquot (1 mL) of the reaction mixture was removed for GPC analysis to confirm the weight average molecular weight of the product iron sucrose complex (about 80000 Daltons).

Step 3—Isolation of the Iron Sucrose Complex

The reaction mixture was concentrated by vacuum distillation at 50 to 60° C. to about 30% of its original volume. Ethanol (about 50 mL) was added to the concentrated reaction mixture at 25° C. with stirring. A dark brown precipitate formed and was collected by filtration. The collected product was purified further by dissolving it in water (10 mL) and subsequently adding ethanol (50 mL) to the dissolved product to precipitate a purified product. The precipitate was collected by filtration, washed with ethanol, and dried under vacuum at about 50° C. The purified product was identified as iron sucrose complex and was analyzed by GPC.

Example 28

Preparation (180 mmol Scale) of Iron Sucrose Complex

Step 1—Preparation of Ferric Hydroxide

Ferric chloride hexahydrate (50 g) was dissolved in deionized water (200 mL) at a temperature of about 20° C. To the stirred ferric chloride solution was added sodium carbonate (33 mL of 30% w/v aqueous solution). The pH of the mixture was monitored using a pH meter. The temperature of the mixture was maintained at about 20° C. Following the addition of sodium carbonate solution, the resulting mixture was dark brown to reddish brown in color. The mixture was allowed to stand for about 30 min., during which time the pH of the reaction mixture was observed to drop to 1.7. Additional sodium carbonate solution was added as the pH of the mixture was monitored. A gelatinous precipitate appeared at a pH of about 3.0. Additional sodium carbonate solution was added until the pH of the mixture reached 4.0, yielding a suspension of ferric hydroxide. Following the addition of sodium carbonate solution, the reaction mixture was allowed to stand for about 10 minutes to allow the precipitate to settle. The precipitated ferric hydroxide was then collected by filtration and washed with water (250 mL). The wet filter cake (about 150 g) was made into a slurry in water (about 200 mL).

Step 2—Preparation of the Iron Sucrose Complex

To a 1000 mL three necked round bottom flask, fitted with reflux condenser and stirrer assembly, was added water (50 mL) and sucrose (300 g). The resulting mixture was heated in an oil bath maintained at about 120° C. for about 20 min. The temperature of the mixture reached about 100-105° C. Sodium hydroxide (about 20 mL, 20% w/v) was added to the heated reaction mixture. Then the slurry of ferric hydroxide prepared in Step 1 was added over about 25 min. The reaction mixture formed a clear, dark brown solution within one minute after the addition of the suspension of ferric hydroxide was completed. Following the addition, the temperature of the reaction mixture was maintained at about 100 to 105° C. for about 2 hrs. The reaction mixture was subsequently cooled to ambient temperature (20 to 25° C.). An aliquot (1 mL) of the reaction mixture was removed for GPC analysis to confirm the weight average molecular weight of the product iron sucrose complex (about 50,000 Daltons). This peak corresponds to the iron sucrose peak obtained on analysis of the marketed iron sucrose in sucrose (VENOFER®), shown in FIG. 3.

Step 3—Isolation of the Iron Sucrose Complex

Ethanol (about 3500 mL) was added into the reaction mixture formed in Step 2, at 25° C. with stirring. A dark brown precipitate formed and was collected by filtration. The collected product was purified further by dissolving it in water (100 mL) and subsequently adding ethanol (500 mL) to the dissolved product to precipitate a purified product. The precipitate was collected by filtration, washed with ethanol, and dried under vacuum at about 50° C. The purified product was identified as iron sucrose complex and was analyzed by GPC, which yielded a weight average molecular weight of about 50,000 Daltons for the principal peak, which was present at greater than 95% purity.

Example 29

Preparation of Iron Sucrose Complex in Injectable Solution

Step 1—Preparation of Ferric Hydroxide

Ferric chloride hexahydrate (5 g, 18.5 mmol) was dissolved in deionized water (20 mL) at a temperature of about 20° C. To the stirred ferric chloride solution was added sodium carbonate 3.3 mL of 30% w/v aqueous solution) in one portion. The pH of the mixture was monitored using a pH meter. The temperature of the mixture was maintained at about 20° C. Following the addition of sodium carbonate, the resulting mixture was dark brown to reddish brown in color. The mixture was allowed to stand for about 30 min., during which time the pH of the reaction mixture was observed to drop to 1.7. Additional sodium carbonate solution (30% w/v aqueous solution) was added as the pH of the mixture was monitored. A gelatinous precipitate appeared at a pH of about 3.0. The addition of the sodium carbonate solution was continued until the pH of the mixture reached 4.0, yielding a suspension of ferric hydroxide. Following the addition of sodium carbonate solution, the reaction mixture was allowed to stand for about 10 minutes to allow the precipitate to settle. The precipitated ferric hydroxide was then collected by filtration and washed with water (25 mL). The wet filter cake (about 15 g) was made into a slurry in water (about 20 mL).

Step 2—Preparation of the Iron Sucrose Complex

To a 100 mL three necked round bottom flask, fitted with reflux condenser and stirrer assembly, was added water for injection (5 mL) and sucrose (15.2 g). The resulting mixture was heated in an oil bath maintained at 120° C. for about 10 min. The temperature of the mixture reached about 100-105° C. Sodium hydroxide (about 2 mL, 20% w/v, made with water for injection) was added to the heated reaction mixture. Then the slurry of ferric hydroxide prepared in Step 1 was added to the sucrose mixture over about 15 min. The reaction mixture formed a clear dark brown solution after the addition of the suspension of ferric hydroxide was completed. Following the addition of the ferric hydroxide slurry, the temperature of the reaction mixture was maintained at about 100 to 105° C. for about 2 hrs. The reaction mixture was subsequently cooled to ambient temperature (20 to 25° C.). An aliquot (1 mL) of the reaction mixture was removed for GPC analysis to confirm the weight average molecular weight of the product iron sucrose complex (about 50,000 Daltons). The reaction mixture was concentrated by vacuum distillation at 35° C. The resulting concentrate was diluted with water to yield a solution containing 20 mg/mL of Ferric iron suitable for injection.

Example: 30

Preparation of Iron Sucrose Complex and Isolation by Freeze Drying

Iron sucrose complex was prepared by the process described in Steps 1 and 2 of Example 1.

After completion of the preparation of iron sucrose complex as in Step 2 of Example 1, the reaction mixture was transferred to a round bottom flask and cooled to about −75° C. to freeze the reaction mixture. The frozen reaction mixture was then freeze dried using a VIRTIS, model 12 EL freeze drying apparatus at a pressure of about 25 millitorr for a time interval of about 12 hours.

Example: 31

Preparation (1.8 mol scale) of Iron Sucrose Complex and Isolation by Centrifugation Step 1—Preparation of Ferric Hydroxide Ferric chloride hexahydrate (500 g) was dissolved in deionized water (2000 mL) at a temperature of about 20° C. To the stirred ferric chloride solution was added sodium carbonate (330 mL of 30% w/v aqueous solution). The pH of the mixture was monitored using a pH meter. The temperature of the mixture was maintained at about 20° C. Following the addition of sodium carbonate solution, the resulting mixture was dark brown to reddish brown in color. The mixture was allowed to stand for about 30 min., during which time the pH of the reaction mixture was observed to drop to 1.7. Additional sodium carbonate solution was added as the pH of the mixture was monitored. A gelatinous precipitate appeared at a pH of about 3.0. Additional sodium carbonate solution was added until the pH of the mixture reached 4.0, yielding a suspension of ferric hydroxide. Following the addition of sodium carbonate solution, the reaction mixture was allowed to stand for about 10 minutes to allow the precipitate to settle. The precipitated ferric hydroxide was then collected by filtration and washed with water (2500 mL). The wet filter cake (about 1500 g) was made into a slurry in water (about 2000 mL).

Step 2—Preparation of the Iron Sucrose Complex

To a 10 liter three-necked round bottom flask, fitted with reflux condenser and stirrer assembly, was added water (500 mL) and sucrose (3000 g). The resulting mixture was heated in an oil bath maintained at about 120° C. for about 20 min. The temperature of the mixture reached about 100-105° C. Sodium hydroxide (about 200 mL, 20% w/v) was added to the heated reaction mixture. Then, the slurry of ferric hydroxide prepared in Step 1 was added to the reaction mixture over a time interval of about 25 min. The reaction mixture formed a clear, dark brown solution within one minute after the addition of the suspension of ferric hydroxide was completed. Following the addition, the temperature of the reaction mixture was maintained at about 100 to 105° C. for about 2 hrs. The reaction mixture was subsequently cooled to ambient temperature (20 to 25° C.). An aliquot (1 mL) of the reaction mixture was removed for GPC analysis to confirm the weight average molecular weight of the product iron sucrose complex (about 49,000 Daltons). This peak corresponds to the iron sucrose peak obtained on analysis of the marketed iron sucrose product (VENOFER®), shown in FIG. 3.

Step 3—Isolation of the Iron Sucrose Complex

Ethanol (about 5000 mL) was added to the reaction mixture formed in Step 2, at 25° C. with stirring. A dark brown precipitate formed. The precipitate was collected by centrifugation at 1500 rpm using a Rousselet-Robatel model RC-30 centrifuge. The mixture containing the precipitated iron sucrose complex was fed to the centrifuge over about 30 min, and the centrifugation was continued for about 30 minutes after the feed was complete.

The collected precipitate was purified further by dissolving it in water (1000 mL) and subsequently adding ethanol (5000 mL) to the dissolved product to precipitate a purified product. The precipitate was collected by centrifugation as described above. The collected purified product was washed with ethanol, and dried under vacuum at about 50° C. The purified product was identified as iron sucrose complex. GPC analysis yielded a weight average molecular weight of about 49,000 Daltons for the principal peak, which was present at greater than 95% purity.

All references cited herein are incorporated by reference. The present invention may be embodied in other specific forms without departing from the spirit or essential attributes thereof and, accordingly, reference should be made to the appended claims, rather than to the foregoing specification, as indication the scope of the invention.

What is claimed is:

1. A process of preparing a co-precipitate comprising iron sucrose complex and sucrose, comprising the steps of:
   (a) reacting ferric hydroxide and sucrose in an aqueous reaction mixture comprising sodium ions, at a selected molar ratio of sucrose to ferric hydroxide, for a selected time interval, at a selected temperature, and at a pH in the range from about 6.5 to about 13;
   (b) isolating iron sucrose complex from the reaction mixture;
   (c) dissolving the isolated iron sucrose complex in an aqueous solvent to form a solution;
   (d) forming a mixture by adding to the solution formed in step (c) at least one water-miscible organic solvent in an amount sufficient to precipitate iron sucrose complex from the solution;
   (e) collecting the purified iron sucrose complex from the mixture formed in step (d);
   (f) dissolving the purified iron sucrose complex product formed in step (e) in an aqueous sucrose solution;
   (g) forming a mixture by adding to the iron sucrose complex solution formed in step (f) at least one water-miscible organic solvent in an amount sufficient to co-precipitate iron sucrose complex and sucrose; and
   (h) collecting the co-precipitate formed in step (g).

2. A process according to claim 1, further comprising the step of drying the co-precipitate.

3. A process according to claim 1, wherein the ratio of purified iron sucrose complex to aqueous sucrose solution is in the range from about 1:0.5 to about 1:10 by weight.

4. A process according to claim 1, wherein the aqueous sucrose solution has a concentration in the range from about 10% to about 50% weight/volume.

5. A process according to claim 1, wherein the water-miscible organic solvent is selected from the group consisting of methanol, ethanol, acetone, tetrahydrofuran, dioxane, acetonitrile and mixtures thereof.

6. A process of preparing an aqueous solution of sucrose and iron sucrose complex, comprising the steps of:
   (a) reacting ferric hydroxide and sucrose in an aqueous reaction mixture comprising sodium ions, at a selected molar ratio of sucrose to ferric hydroxide, for a selected time interval, at a selected temperature, and at a pH in the range from about 6.5 to about 13;
   (b) isolating iron sucrose complex from the reaction mixture;
   (c) dissolving the isolated iron sucrose complex in an aqueous solvent to form a solution;
   (d) forming a mixture by adding to the solution formed in step (c) at least one water-miscible organic solvent in an amount sufficient to precipitate iron sucrose complex, from the solution;
   (e) collecting the purified iron sucrose complex from the mixture formed in step (d);
   (f) dissolving the purified iron sucrose complex product formed in step (e) in an aqueous sucrose solution;
   (g) forming a mixture by adding to the iron sucrose complex solution formed in step (f) at least one water-miscible organic solvent in an amount sufficient to co-precipitate iron sucrose complex and sucrose;
   (h) collecting the co-precipitate formed in step (g); and
   (i) dissolving the collected co-precipitate in water.

7. A process of preparing a co-precipitate comprising iron sucrose complex and sucrose, the process comprising the steps of:
   (a) providing a reaction mixture comprising a ferric salt dissolved in an aqueous medium;
   (b) adding to the reaction mixture a first base in an amount in the range from about 1 to about 2 equivalents based on the amount of ferric salt;
   (c) allowing the reaction mixture to equilibrate for a time interval in the range from about 10 to about 60 minutes;
   (d) forming a mixture by adding sucrose to the equilibrated reaction mixture of step (c) in a selected molar ratio based on the ferric salt;
   (e) heating the mixture formed in step (d) to a first temperature;

(f) forming a mixture by adding to the heated mixture formed in step (e) a second base in an amount sufficient to adjust the pH of the reaction mixture to a selected pH;

(g) heating the mixture formed in step (f) at a second temperature for a selected time interval;

(h) after the selected time interval, cooling the reaction mixture to a temperature in the range of from about 20° to about 30° C.; and (i) isolating the co-precipitate from the cooled reaction mixture.

8. A process according to claim 7, wherein selected molar ratio of sucrose to the ferric salt is in the range from about 2:1 to about 50:1.

9. A process according to claim 7, wherein the step of isolating the co-precipitate comprises the steps of:

(a) forming a mixture by adding to the cooled reaction mixture at least one water-miscible organic solvent in an amount sufficient to co-precipitate iron sucrose complex and sucrose;

(b) collecting the co-precipitate formed in step (a); and optionally (c) drying the collected co-precipitate.

10. A process according to claim 9, wherein the cooled reaction mixture is optionally concentrated prior to the addition of the water-miscible organic solvent.

11. A process according to claim 7, wherein the first temperature is a temperature in the range of from about 60° C. to about 90° C.

12. A process according to claim 7, wherein the second temperature is a temperature in the range of from about 75° C. to about 120° C.

13. A process according to claim 7, wherein the first and second bases are selected from the group consisting of alkali metal carbonates, alkali metal bicarbonates, alkali metal hydroxides, water soluble amines, and combinations thereof.

* * * * *